United States Patent
Fan et al.

(10) Patent No.: US 9,798,304 B2
(45) Date of Patent: Oct. 24, 2017

(54) PRODUCTION PROCESS MONITORING SYSTEM AND CONTROL METHOD THEREFOR

(75) Inventors: Shun Jie Fan, Beijing (CN); Xian Tao Meng, Langfang (CN)

(73) Assignee: Siemens Aktiengesellschaft, Munich (DE)

( * ) Notice: Subject to any disclaimer, the term of this patent is extended or adjusted under 35 U.S.C. 154(b) by 546 days.

(21) Appl. No.: 14/353,181

(22) PCT Filed: Oct. 28, 2011

(86) PCT No.: PCT/CN2011/081523
§ 371 (c)(1),
(2), (4) Date: Jun. 24, 2014

(87) PCT Pub. No.: WO2013/060027
PCT Pub. Date: May 2, 2013

(65) Prior Publication Data
US 2014/0330398 A1 Nov. 6, 2014

(51) Int. Cl.
*G05B 15/02* (2006.01)
*C12M 1/36* (2006.01)
(Continued)

(52) U.S. Cl.
CPC .......... *G05B 15/02* (2013.01); *C12M 23/58* (2013.01); *C12M 41/26* (2013.01); *C12M 41/34* (2013.01); *C12M 41/36* (2013.01); *C12M 41/48* (2013.01)

(58) Field of Classification Search
CPC ....... G05B 15/02; C12M 23/58; C12M 41/34; C12M 41/36; C12M 41/26; C12M 41/48
See application file for complete search history.

(56) References Cited

U.S. PATENT DOCUMENTS

2004/0250700 A1* 12/2004 Renaud .................. B09B 1/00
100/38
2005/0158701 A1 7/2005 West
(Continued)

FOREIGN PATENT DOCUMENTS

CN 1201826 12/1998
CN 2570287 9/2003
(Continued)

OTHER PUBLICATIONS

International Search Report dated Jan. 17, 1012.

*Primary Examiner* — Jill Warden
*Assistant Examiner* — Matthew Krcha
(74) *Attorney, Agent, or Firm* — Cozen O'Connor (57) ABSTRACT

A production process monitoring system is used to monitor a set of production parameters in a production process of a plurality of production units that perform parallel production operation. The production units comprise at least one reference production unit and at least one distribution production unit. The reference production unit comprises a first sensor, a second sensor, and a reference control unit. The distribution production unit comprises a second sensor and a distribution controller. The first and second sensors of the reference production unit is configured to monitor a first and second parameters in the production parameters in the reference production unit and output a first and second signals corresponding to the first and second parameters. The second sensor of the distribution production unit is configured to monitor the second parameter in the distribution production unit and output a second parameter distribution signal corresponding to the second parameter.

15 Claims, 5 Drawing Sheets

(51) Int. Cl.
*C12M 1/00* (2006.01)
*C12M 1/34* (2006.01)

(56) References Cited

U.S. PATENT DOCUMENTS

| | | |
|---|---|---|
| 2006/0216790 A1 | 9/2006 | Knudsen |
| 2008/0160591 A1 | 7/2008 | Willson et al. |
| 2009/0011492 A1 | 1/2009 | Berzin |
| 2010/0151558 A1 | 6/2010 | Alianell et al. |
| 2012/0107921 A1 | 5/2012 | Willson et al. |

FOREIGN PATENT DOCUMENTS

| | | |
|---|---|---|
| CN | 1473629 | 2/2004 |
| CN | 101750989 | 6/2010 |
| CN | 102131383 | 7/2011 |
| DE | 103 54 406 | 6/2005 |
| WO | WO 2005/035748 | 4/2005 |
| WO | WO 2009/129654 | 10/2009 |
| WO | WO 2010/002745 | 1/2010 |
| WO | WO 2010/142004 | 12/2010 |

\* cited by examiner

PRODUCTION PROCESS MONITORING SYSTEM AND CONTROL METHOD THEREFOR

CROSS-REFERENCE OF RELATED APPLICATIONS

This is U.S. national stage of PCT Application No. PCT/CN2011/081523, filed on Oct. 28, 2011, which is hereby incorporated herein in its entirety by reference.

FIELD OF THE INVENTION

The present invention relates to a monitoring and control system. Specifically, the present invention relates to a monitoring and control system specific to the production parameters, such as pH value, dissolved oxygen and biomass concentration, in a plurality of production units (e.g., closed photobioractors for large-scale culture of algae) which perform parallel operation. The present invention also relates to a control method for a monitoring and control system, and the control method may also be applied to the monitoring and control of other large-scale industrial production based on production parameters.

DESCRIPTION OF THE RELATED ART

Unicellular microalgae organisms are capable of transforming sunlight, water and carbon dioxide into algae biomass (later referred to as "algae"), and such algae can be collected and processed to obtain available products such as biofuels; therefore, it is considered that large-scale culture and processing of algae is one of the effective measures to solve the global environmental and energy issues.

Microalgae can be cultured in open ponds, with advantages of simple operation, low cost of production, etc.; however, disadvantageously, the yield of algae is low, water in a pond is easy to evaporate, and the culture environment of microalgae is easily contaminated. Microalgae can also be cultured in a flat, tubular or cylindrical closed photobioreactor (later referred to as "reactor"), which can improve the yield of algae and protect the culture environment from contamination. The growth of algae needs light and gas, but the volume of a single reactor is limited, with the area of a reactor hardly exceeding a few hundred square meters, which means a large-scale microalgae culture production process needs the construction of thousands of reactors in parallel production. The construction, operation and maintenance of reactors need huge capital investments.

In order to improve the yield of algal biomass, each reactor should be effectively monitored. Optimal culture conditions for the growth of algae can be provided by monitoring the reactor parameters of the environment for the growth of algae and for adjusting the operating parameters, thereby ensuring the growth and yield of algae. Due to the complex process of photosynthesis of algae, temperature, pH value, dissolved oxygen, biomass concentration, etc., inside the reactor should be monitored independently. Therefore, the cost of monitoring equipment accounts for a considerable part of the cost of a reactor.

Currently, each reactor requires independently installed measuring instruments, such that the entire algae production process requires a number of sensors for pH value, dissolved oxygen, biomass concentration, etc. For example, if an algae culture system comprises 4,000 reactors (the floor area of each reactor is 500-1,000 m$^2$) and even if each reactor is only provided with a pH sensor, a dissolved oxygen sensor and a biomass concentration sensor, the entire culture system requires 12,000 sensors. Here, pH and dissolved oxygen sensors have higher costs and need frequent calibration and maintenance. However, if the reactors are disposed in a non-monitoring open-loop control mode in order to reduce the cost of the sensors, the algae yield of the entire culture system will be reduced, which also indirectly causes an increase in algae production cost.

In order to reduce the number of sensors used in the culture system, some literatures disclose monitoring and control models for reactors. For example, "Biochemical Engineering Journal, 2003 Vol. 14: P51-65 and "Online estimation of stirred-tank microalgal photobioreactor cultures based on dissolved oxygen measurement" discusses using a model-based observer (also referred to as soft-sensors) and a model-based control system. Although these methods reduce the use of sensors, the development and maintenance of soft-sensors are complicated, and the reliability and effectiveness of soft-sensors may decrease with use.

SUMMARY OF THE INVENTION

An object of the present invention is to provide a production process monitoring system, to reduce the number of sensors used in the entire monitoring system. Another object of the present invention is to provide a control method for a production process monitoring system.

The present invention provides a production process monitoring system for monitoring the production parameters of the production process of a plurality of production units which parallel production operation. The production parameters comprise at least a first parameter and a second parameter, and the production unit comprises a reference production unit and at least one distribution production unit.

In one embodiment, a production process monitoring system monitors the production parameters of the production process of a plurality of production units which parallel production operation. The production unit comprises at least one reference production unit and at least one distribution production unit. The reference production unit is at least provided with a first sensor and a second sensor. The first sensor is used to monitor a first parameter in the production parameters of the reference production unit and output a first signal corresponding to the first parameter of the reference production unit. The second sensor is used to monitor a second parameter in the reference production unit and output a second parameter reference signal corresponding to the second parameter of the reference production unit.

A reference control unit may input a set value and the first signal, and output a first control amount, which may control the first parameter in the reference production unit, to the reference production unit according to the set value and the received first signal. The distribution production unit is provided with a second sensor that is used to monitor the second parameter in the distribution production unit, and outputs a second distribution signal corresponding to the second parameter of the distribution production unit. A distribution controller may receive an input signal comprising the first control amount, the second parameter reference signal and the second distribution signal, and output a distribution control amount to the distribution production unit. The distribution controller may control a ratio of the distribution control amount to the first control amount to change according to a ratio of the second distribution signal to the second parameter reference signal.

The production process monitoring system avoids installing a first parameter sensor on each distribution production unit of the entire monitoring system, thereby greatly reducing the cost of the monitoring system during the production process, and also reducing the maintenance and operation costs of the entire system due to a reduced number of sensors in use.

In a further embodiment of the monitoring system of the production process, the production unit also comprises a correction production unit provided with a first sensor and a second sensor. The first sensor may monitor a first parameter in the correction production unit and output a third signal corresponding to the first parameter, and the second sensor may monitor a second parameter in the correction production unit and output a second parameter correction signal corresponding to the second parameter. The monitoring system also comprises a correction unit and a correction controller. The correction unit may output a correction signal according to the received third signal and set value. The correction controller may output a correction control amount to the correction production unit according to the received correction signal, the first control amount, the second parameter reference signal and the second parameter correction signal. The correction controller may control a ratio of the correction control amount to the first control amount to change according to a ratio of the second parameter correction signal to the second parameter reference signal.

In another embodiment of the monitoring system of the production process, a computational formula of the correction control amount is:

$$C_C = (K_m \times S_{2C}/S_{2S}) \times C_1,$$

and a computational formula of the distribution control amount is:

$$C_D = (K_m \times S_{2D}/S_{2S}) \times C_1.$$

By setting the correction production unit and the corresponding correction unit and correction controller, the control accuracy of the first parameter in the correction production unit and the distribution production unit can be improved through the correction signal in each control loop.

In another embodiment of the monitoring system of the production process, the reference control unit comprises a reference comparator and a reference controller. The reference comparator may output a first difference signal of the difference between the set value and the received first signal. The reference controller determines the first control amount according to the first difference signal.

In another embodiment of the monitoring system of the production process, a computational formula of the correction signal is:

$$K_m = K_{m-1} + K_C \left( (e_m - e_{m-1}) + \frac{\Delta t}{\tau_I} e_m \right),$$

where subscript 'm' represents the $m^{th}$ control loop in which the monitoring system is located, $\Delta t$ represents the control cycle, and 'e' is the difference between the set value and the third signal ($S_{1S} - S_3$). $K_C$ and $\tau_I$ are set parameters of the correction production unit.

In another embodiment of the monitoring system of the production process, the correction unit comprises a correction comparator and a corrector. The correction comparator may input a third difference signal of the difference between the set value and the received third signal. The corrector determines the correction control amount according to the third difference signal.

In another embodiment of the monitoring system of the production process, the production process is the culture of algae, and the production unit is a photobioreactor.

In another embodiment of the monitoring system of the production process, the first parameter is the pH value of the algae conditioned medium in the photobioreactor, the second parameter is the biomass concentration of the algae conditioned medium in the photobioreactor, the first control amount and the distribution control amount are the volume of carbon dioxide introduced into the algae conditioned medium, and the pH value of the algae conditioned medium is controlled by the volume of carbon dioxide introduced therein.

In another embodiment of the monitoring system of the production process, the first control amount, the distribution control amount and the correction control amount are the volume of carbon dioxide introduced into the algae conditioned medium, and the pH value of the algae conditioned medium is controlled by the volume of carbon dioxide introduced therein.

In another embodiment of the monitoring system of the production process, the first parameter is the dissolved oxygen level of the algae conditioned medium in the photobioreactor, the second parameter is the biomass concentration of the algae conditioned medium in the photobioreactor, the first control amount and the distribution control amount are the volume of air introduced into the algae conditioned medium, and the dissolved oxygen level of the algae conditioned medium is controlled by the volume of air introduced therein.

In another embodiment of the monitoring system of the production process, the first control amount, the distribution control amount and the correction control amount are the volume of air introduced into the algae conditioned medium, and the dissolved oxygen level of the algae conditioned medium is controlled by the volume of air introduced therein.

In another embodiment of the monitoring system of the production process, a sensor for measuring biomass concentration is a near-infrared light sensor.

The present invention also provides a control method for the monitoring system of the production process. The control method includes (i) setting a set value, control cycle, and production cycle of the production process; (ii) performing sampling at the first sensor and the second sensor of the reference production unit and the second sensor of the distribution production unit, and outputting, at the first sensor of the reference production unit, the first signal to the reference control unit, outputting, at the second sensor of the reference production unit, the second reference signal to the distribution controller, and outputting, at the second sensor of the distribution production unit, the second distribution signal to the distribution controller; (iii) calculating, at the reference control unit, the first control amount according to the set value and the first signal and outputting the same to the reference production unit and the distribution controller, and calculating, at the distribution controller, the distribution control amount according to the first control amount, the second distribution signal and the second reference signal and outputting the same to the distribution production unit; (iv) controlling, at the reference production unit, the first parameter therein through the first control amount, and controlling, at the distribution production unit, the first parameter therein through the distribution control amount;

(v) determining whether it reaches the production cycle of the production process or not, and if yes, ending the monitoring process, or else proceeding to step (vi); and determining whether it reaches the control cycle or not, and if yes, returning to step (ii), or else returning to step (iv).

The present invention also provides another control method for the monitoring system of the production process. The control method includes: (i) setting a set value, control cycle, and production cycle of the production process; (ii) performing sampling at the first sensor and second sensor of the reference production unit, the first sensor and the second sensor of the correction production unit, and the second sensor of the distribution production unit, and outputting, at the first sensor of the reference production unit, the first signal to the reference control unit, outputting, at the second sensor of the reference production unit, the second reference signal to the correction controller and the distribution controller, outputting, at the first sensor of the correction production unit, the third signal to the correction unit, outputting, at the second sensor of the correction production unit, the second parameter correction signal to the correction controller, and outputting, at the second sensor of the distribution production unit, the second distribution signal to the distribution controller; (iii) calculating, at the reference control unit, according to the set value and the first signal to obtain the first control amount and outputting the same to the reference production unit, calculating, at the correction controller and the distribution controller, and the corrector, according to the set value and the third signal to obtain the correction signal and outputting the same to the correction controller and the distribution controller; (iv) calculating, at the correction controller, according to the correction signal, the first control amount, the second reference signal and the second parameter correction signal to obtain the correction control amount and outputting the same to the correction production unit, and calculating, at the distribution controller, according to the first control amount, the correction signal, the second distribution signal and the second reference signal to obtain the distribution control amount and outputting the same to the distribution production unit; (v) controlling, at the reference production unit, the first parameter therein through the first control amount, controlling, at the distribution production unit, the first parameter therein through the distribution control amount, and controlling, at the correction production unit, the first parameter therein through the correction control amount; (vi) determining whether it reaches the production cycle of the production process or not, and if yes, ending the monitoring process, or else proceeding to step (vii); and (vii) determining whether it reaches the control cycle or not, and if yes, returning to step (ii), or else returning to step (v).

For the above-mentioned monitoring system control method in an embodiment, the control cycle is in a range of 1 s to 1 h.

BRIEF DESCRIPTION OF THE DRAWINGS

The following figures are only for illustrative description and explanation of the present invention and are not to limit the scope of the present invention.

The preferred embodiments will be described below with reference to the accompanying drawings in a clear and understandable way, and the characteristics, technical features, advantages and implementations of the production process monitoring system and the control method therefor will be further described.

DETAILED DESCRIPTION OF THE PRESENTLY PREFERRED EMBODIMENTS

In order to understand the technical features, objects and effects of the present invention more clearly, particular embodiments of the present invention are described here with reference to the accompanying drawings, in which, like numerals in the figures represent the same parts or parts with a similar structure but the same function.

To make the figures look concise, only parts related to the present invention are illustratively shown in each of the figures, and they do not represent the practical structure of the product. In addition, to make the figures look concise and easy to understand, in some figures, only one of components with the same structure or function is illustratively drawn or marked.

Figure 1:
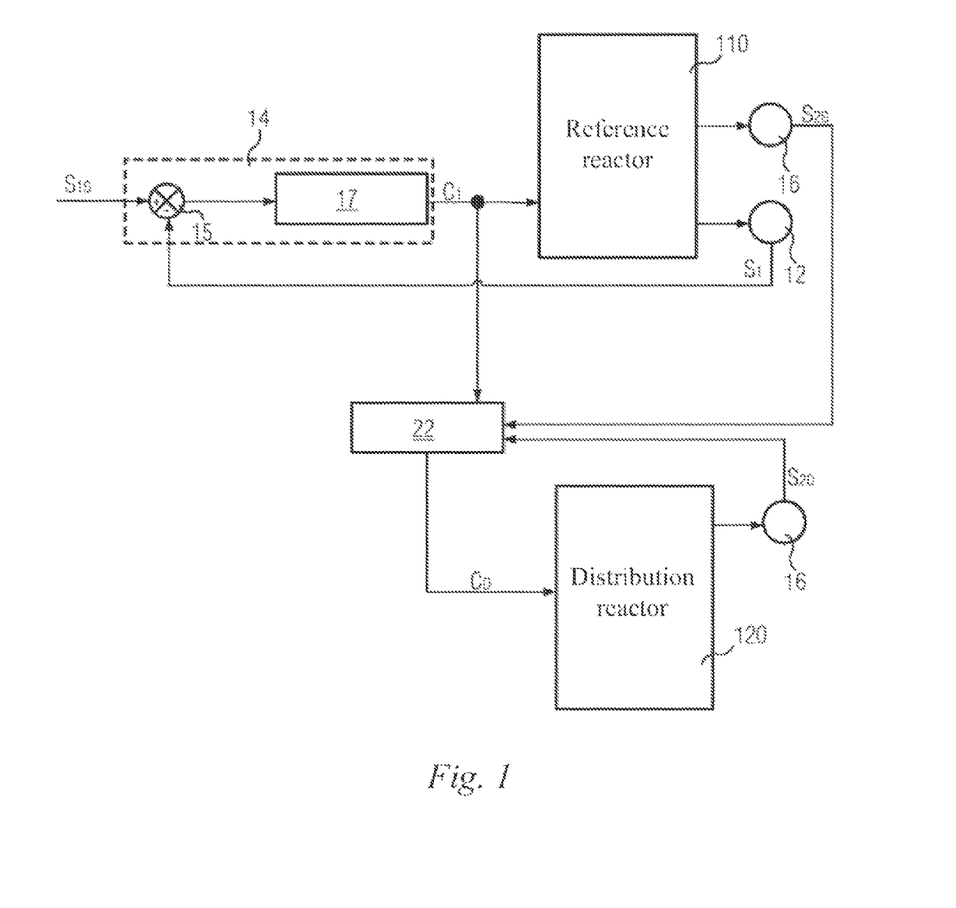
FIG. 1 is a block diagram showing a production process monitoring system in combination with a monitoring system for the culture of algae in accordance with one embodiment of the present invention.

FIG. 1 is used to illustrate a production process monitoring system of the present invention in combination with a monitoring system for the culture of algae. In the production process of the culture of algae, the production unit for the culture of algae is a photobioreactor (later referred to as "reactor"). The large-scale culture process of algae generally comprises a number of reactors (for example, 4,000), with multiple reactors with similar surroundings (for example, 100) being defined as region A, and the monitoring system herein is used in the region A. However, the entire culture process may comprise multiple such regions, and each region is installed with a monitoring system according to the present invention.

An optional reactor in the monitor for the culture of algae is used as reference production unit 110, i.e., the reference photobioreactor (later referred to as "reference reactor 110"); and then another photobioreactor in the same region is selected to be used as distribution production unit 120, i.e., the distribution photobioreactor (later referred to as "distribution reactor 120"). It should be noted that in other embodiments of the present invention, the number of reference production unit 110 and distribution production unit 120 may be selected to be at least one.

There are many production parameters that influence the algae culture production process, comprising pH value of algae conditioned medium (later referred to as "pH value"), biomass concentration of conditioned medium (later referred to as "biomass concentration") and dissolved oxygen of conditioned medium (later referred to as "dissolved oxygen") for example, in which the pH value or dissolved oxygen are defined as a first parameter, and the biomass concentration is defined a second parameter. The first sensor 12 is a pH sensor (in other embodiments of the present invention, the first sensor 12 may also use a sensor for monitoring other production parameters, such as a dissolved oxygen sensor), the second sensor 16 is a biomass concentration sensor (such as the first sensor 12, in other embodiments, the second sensor 16 may also use a sensor for other production parameters).

In the production process of the culture of algae, the biomass concentration reference signal $S_{2S}$ corresponds to the biomass of algae in the reactor. The higher the signal value, the larger the required volume of carbon dioxide $C_1$, thereby ensuring the photosynthesis of the algae organism. The first signal $S_1$ reflects the pH value of the culture solution in the reactor, with the pH value influenced by the introduced volume of carbon dioxide $C_1$, i.e., the larger the volume of introduced carbon dioxide $C_1$, the higher the pH value of the culture solution in the reactor. Here, the pH value of the culture solution in the reactor is selected to control the volume of carbon dioxide $C_1$, which is a common means for the culture of algae.

As shown in FIG. 1, the monitoring system for the culture of algae comprises a pH sensor 12, two biomass concentration sensors 16, a reference control unit 14 and a distribution controller 22. Though the figure only shows a reference reactor and a distribution reactor, and the monitoring system used in a region for the culture of algae may comprise several reference reactors and distribution reactors. Here, the reference reactor 110 and the distribution reactor 120 simultaneously perform the culture of algae in parallel. The monitoring system may monitor the pH value and biomass concentration in the reference reactor 110 and the biomass concentration of algae conditioned medium in the distribution reactor 120, and control the pH value in the reference reactor 110 and the distribution reactor 120.

Here, as shown in FIG. 1, the reference control unit 14 comprises a reference comparator 15 and a reference controller 17. The reference comparator 15 may input the first signal $S_1$ and the set value $S_{1S}$, and output the difference $S_{1S}-S_1$ between the first signal $S_1$ and the set value $S_{1S}$ to the reference controller 17. The reference controller 17 controls the value of the first control amount $C_1$ according to the difference $S_{1S}-S_1$ between the first signal $S_1$ and the set value $S_{1S}$, wherein the first control amount $C_1$ represents the volume of carbon dioxide gas in the algae conditioned medium of the reference reactor 110.

Furthermore, in this embodiment, the reference reactor 110 is provided with a pH sensor 12, a biomass concentration sensor 16 and a reference control unit 14. The pH sensor 12 may monitor the pH value of the algae conditioned medium in the reference reactor 110, and output the first signal $S_1$ indicating the pH value to the reference comparator 15 of the reference control unit 14. The biomass concentration sensor 16 may monitor the biomass concentration of the algae conditioned medium in the reference reactor 110, and output the biomass concentration reference signal $S_{2S}$ indicating the biomass concentration to the distribution controller 22.

The reference control unit 14 is preset with a set value $S_{1S}$ that indicates the optimized pH value in the algae conditioned medium. The reference control unit 14 may output the first control amount $C_1$ to the reference reactor 110 (e.g., the volume of carbon dioxide gas introduced into the algae conditioned medium) by adjusting the volume of carbon dioxide gas introduced into the algae conditioned medium of the reference reactor 110. The first control amount $C_1$, the pH signal $S_1$ (i.e., the pH value), and the biomass concentration reference signal $S_{2S}$ of the algae conditioned medium in the reference reactor 110 can be adjusted.

The reference control unit 14 may compare the deviation of the first signal $S_1$ from the set value $S_{1S}$, so as to control the volume of carbon dioxide gas introduced into the algae conditioned medium, and may further reduce the deviation of the first signal $S_1$ from the set value $S_{1S}$, if further reduction is warranted. For example, the reference control unit 14 may reduce the deviation of the first signal $S_1$ from the set value $S_{1S}$ by means of PID (proportion integration differentiation) control.

The distribution reactor 120 is installed with a biomass concentration sensor 16 and a distribution controller 22. The biomass concentration sensor 16 may monitor the biomass concentration of the algae conditioned medium in the distribution reactor 120, and output the biomass concentration distribution signal $S_{2D}$ indicating the value of biomass concentration to the distribution controller 22. The distribution controller 22 may also receive the first control amount $C_1$ output from the reference control unit 14 and the biomass concentration reference signal $S_{2S}$ output from the biomass concentration sensor 16 in the reference reactor 110, and output a distribution control amount $C_D$ to the distribution production unit 120 (e.g., the volume of carbon dioxide gas introduced into the algae conditioned medium). The distribution controller 22 may adjust the pH value of the algae conditioned medium by adjusting the volume of carbon dioxide gas introduced into the conditioned medium.

The biomass concentration of the conditioned medium in the reference reactor 110 and the distribution reactor 120 indicates the cell count of algae. Because algae different in biomass are different in demand of the volume of carbon dioxide gas, the pH sensor 12 monitors the volume of carbon dioxide gas introduced into the reference reactor 110, and forms closed-loop control together with the reference control unit 14, to ensure that the volume of carbon dioxide gas introduced into the reference reactor 110 meets the demand of the algae in the count, and therefore, the distribution control amount $C_D$ is controlled based on the first control amount $C_1$ and according to the ratio of the biomass concentrations in the reference reactor 110 and the distribution reactor 120, such that the ratio $C_D/C_1$ of the distribution control amount $C_D$ to the first control amount $C_1$ is in direct proportion to the ratio $S_{2D}/S_{2S}$ of the biomass concentration distribution signal $s_{2D}$ to the biomass concentration reference signal $S_{2S}$, i.e., according to the formula:

$$C_D=(K \times S_{2D}/S_{2S}) \times C_1,$$

which calculates the value of the distribution control amount $C_D$, where K is a proportionality coefficient, generally being 1, and the magnitude of the value of K may also be finely adjusted manually to adjust the value of the distribution control amount $C_D$.

The monitoring system for the culture of algae may further be added with multiple distribution reactors, all of which are monitored and controlled as described above. In addition, the monitoring system for the culture of algae may also comprise multiple reference reactors, all of these reference reactors independently obtain the first control amount $C_1$ corresponding to different reference reactors according to the pH values of the algae conditioned media thereof; and simultaneously, the biomass concentration sensors installed on the reference reactors independently output biomass concentrations $S_{2S}$ corresponding to the reference reactors, and the distribution controller 22 may receive the first control amount $C_1$ and the biomass concentrations $S_{2S}$ output from the reference control unit in each reference reactor, and obtain the averages of the first control amount $C_1$ and the biomass concentrations $S_{2S}$ for use as a control basis of the distribution control amount $C_D$.

For the monitoring system for the culture of algae, especially for the situation where the monitoring system comprises a number of reactors, multiple reactors in a region can be monitored as one virtual reactor. The control on the pH value of algae conditioned medium may be accomplished by only taking one of the photobioreactors as a reference reactor and other photobioreactors as distribution reactors and by only monitoring the pH value and biomass concentration of the reference reactor while monitoring the biomass concentration of each distribution reactor, so as to avoid installing an expensive pH sensor on each distribution reactor in the entire monitoring system, thereby greatly reducing the cost of the monitoring system during the culture of algae, and also reducing the maintenance and operation costs of the entire system due to a reduced number of sensors in use.

At the same time, the control on pH value in the distribution reactor is a ratio control having an adaptive ability and may adjust the pH value in the distribution reactor by adjusting the ratio of the distribution control amount $C_D$ to the first control amount $C_1$, which is simple and easy to operate and can obviate the use of a complex microalgae mathematical model to simulate the photobioreactor. The control mode of the distribution control amount is not limited to the above-mentioned ratio control, and may also use other control algorithms.

Although the above-mentioned embodiments take the monitoring system for the culture of algae for example, they may also be applied to the culture of algae using a plurality of parallel open ponds. The monitoring system may also be applied to control the production parameters in multiple production units which perform a parallel operation, for example, chemical industry, petrochemical, foods, semiconductor industry, etc.

Figure 4:
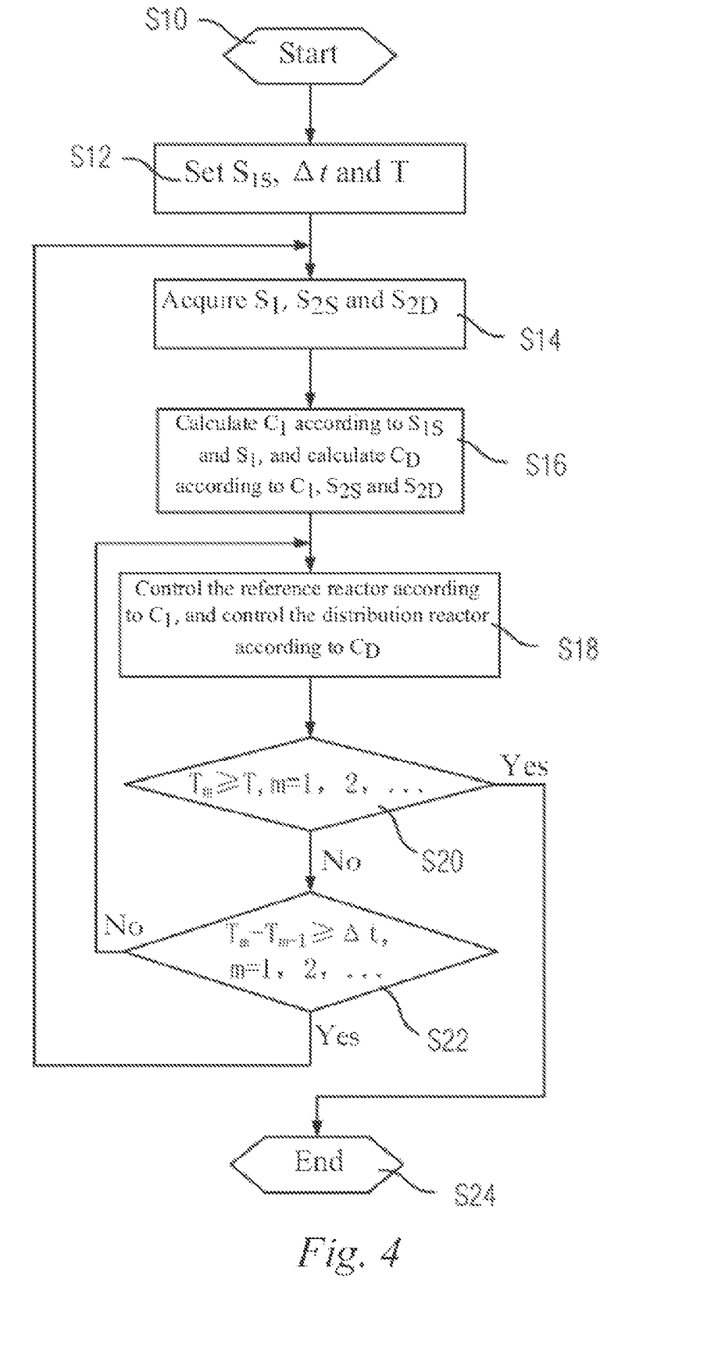
FIG. 4 is a control flowchart of the monitoring system shown in FIG. 1.

FIG. 4 is a control flowchart of the monitoring system shown in FIG. 1. As shown in FIG. 4, the control flow of the monitoring system for the culture of algae starts from step S10. In step S12, the set value $S_{1S}$, the control cycle $\Delta t$, and the production cycle T of the entire production process are set. In one embodiment of the culture of algae, the set value $S_{1S}$ is set to 7.0, the control cycle $\Delta t$ is set to one minute, and the production cycle T is set to 200 hours.

In step S14, the pH sensor 12 and the biomass concentration sensor 16 of the reference reactor 110, and the biomass concentration sensor 16 of the distribution reactor 120 perform sampling, and the pH sensor 12 of the reference reactor 110 outputs the first signal $S_1$ corresponding to the pH value in the reference reactor 110 to the reference control unit 14, the biomass concentration sensor 16 of the reference reactor 110 outputs the biomass concentration reference signal $S_{2S}$ corresponding to the biomass concentration in the reference reactor 110 to the distribution controller 22, and the biomass concentration sensor 16 of the distribution reactor 120 outputs the biomass concentration distribution signal $S_{2D}$ corresponding to the biomass concentration in the distribution reactor 120 to the distribution controller 22.

In step S16, the reference control unit 14 calculates according to the set value $S_{1S}$ and the first signal $S_1$ to obtain the first control amount $C_1$, and transmits the first control amount $C_1$ to the reference reactor 110 and the distribution controller 22, and the distribution controller 22 calculates according to the first control amount $C_1$, the second distribution signal $S_{2D}$ and the second reference signals $S_{2S}$ to obtain the distribution control amount $C_D$, and transmits the distribution control amount $C_D$ to the distribution reactor 120, then proceed to step S18.

In step S18, the reference reactor 110 controls the first parameter therein through the first control amount $C_1$, and the distribution reactor 120 controls the first parameter therein through the distribution control amount $C_D$.

In step S20, the system determines whether it reaches the production cycle T of the production process or not, and if the production cycle is reached, the monitoring process ends at S24. If the production cycle is not yet reached, the monitoring process proceeds to step S22.

In step S22, the system determines whether it reaches the control cycle $\Delta t$, and if the control cycle is reached, the monitoring process returns to step S14. If the control cycle is not yet reached, the monitoring process returns to step S18.

Figure 2:
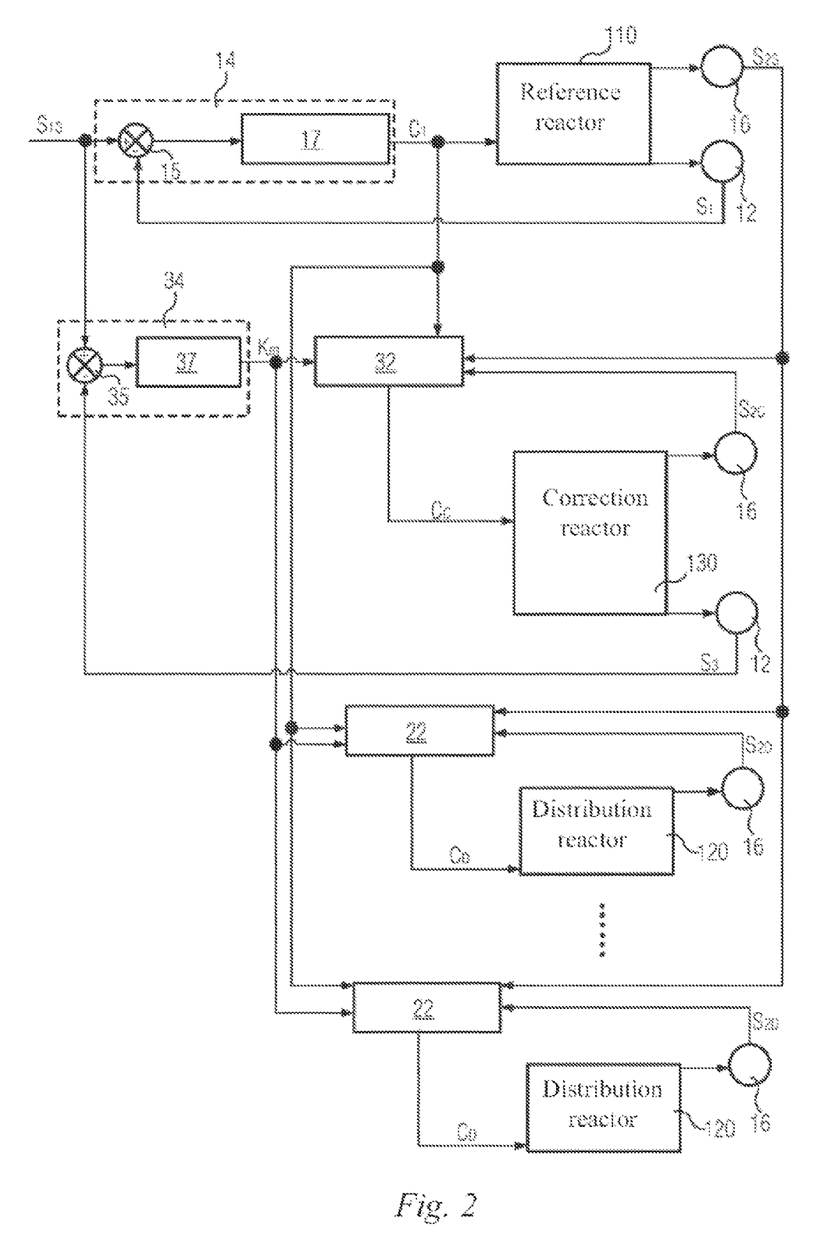
FIG. 2 is a block diagram showing a production process monitoring system in combination with a monitoring system for the culture of algae in accordance with one embodiment of the present invention.

FIG. 2 is a principle schematic view of another embodiment of the monitoring system for the culture of algae. The structure in FIG. 2 which is the same as in FIG. 1 is not described again in detail. In this embodiment, the monitoring system also comprises a correction production unit 130 (later referred to as "correction reactor 130"), which is another reactor in the same region of the reference reactor 110 and the distribution reactor 120. Similarly, the correction reactor 130 is provided with a pH sensor 12 and a biomass concentration sensor 16. The monitoring system also comprises a correction controller 32 and a correction unit 34. More particularly, as shown in FIG. 2, the correction unit 34 comprises a correction comparator 35 and a corrector 37. The correction comparator 35 may input the third signal $S_3$ and the set value $S_{1S}$, and output the difference $S_{1S}-S_3$ between the set value $S_{1S}$ and the third signal $S_3$ to the corrector 37, and the corrector 37 may obtain $K_m$ according to the difference $S_{1S}-S_3$ between the set value $S_{1S}$ and the third signal $S_3$.

In the monitoring system for the culture of algae, the pH sensors in the reference reactor, the correction reactor and the distribution reactor may be substituted by dissolved oxygen sensors. The dissolved oxygen values in the reference reactor, the correction reactor and the distribution reactor may be controlled through the control of the volume of air introduced into the reference reactor, the correction reactor and the distribution reactor, wherein the larger the volume of air, the higher the dissolved oxygen. The control of the volume of air introduced into the reference reactor, the correction reactor and the distribution reactor may refer to the control method of the volume of introduced carbon dioxide in the reference reactor, the correction reactor and the distribution reactor (i.e., the control of the pH value of the algae conditioned medium), which is not described again here in detail. In addition, the reference reactor, the correction reactor and the distribution reactor of the monitoring system for the culture of algae may be provided with the pH sensor and the dissolved oxygen sensor at the same time, so as to control the dissolved oxygen and pH value in the reference reactor, the correction reactor and the distribution reactor simultaneously.

In one embodiment of the monitoring system for the culture of algae, the biomass concentration sensor is a near-infrared light sensor. The pH sensor 12 may measure the pH value of the conditioned medium in the correction reactor 130, and output the third signal $S_3$ corresponding to the pH value to the correction unit 34. The biomass concentration sensor 16 may measure the biomass concentration of the conditioned medium in the correction reactor 130, and output the biomass concentration correction signal $S_{2C}$ to the correction controller 32. The correction unit 34 calculates according to the input third signal $S_3$ and the set value $S_{1S}$, the operation of 35 and 37, to output a correction signal $K_m$ to the correction controller 32, in which a computational formula of $K_m$ is defined as:

$$K_m = K_{m-1} + K_c\left((e_m - e_{m-1}) + \frac{\Delta t}{\tau_I}e_m\right),$$

where subscript m represents the $m^{th}$ control loop in which the monitoring system is located, where m is larger than 1; $\Delta t$ represents the control cycle; 'e' is the difference ($S_{1S}-S_3$) between the set value and the third signal; $K_c$ and $\tau_1$ are set parameters of the correction reactor, and values of $K_c$ and $\tau_1$ may be determined by on-site debugging in the actual operation. $K_m$ is a value calculated in each control cycle by the correction unit, i.e., the above-mentioned adaptive control of proportionality coefficient K, where $K=K_m$.

The correction controller 32 may calculate a correction control amount $C_C$ according to the input correction signal $K_m$, the first control amount $C_1$, the biomass concentration correction signal $S_{2C}$ and the biomass concentration reference signal $S_{2S}$ and output the same to the correction reactor 130, to control the volume of carbon dioxide introduced into the correction reactor 130, in which a computational formula of the correction control amount $C_C$ is defined as:

$$C_C = (K_m \times S_{2C}/S_{2S}) \times C_1$$

The correction signal $K_m$ output from the correction unit 34 may also be input into the distribution controller 22 of the distribution reactor 120, and the distribution controller 22 calculates the output distribution control amount $C_D$ according to the correction signal $K_m$, the first control amount $C_1$, the biomass concentration reference signal $S_{2S}$ and the biomass concentration distribution signal $S_{2D}$, in which a computational formula of the distribution control amount $C_D$ is defined as:

$$C_D = (K_m \times S_{2D}/S_{2S}) \times C_1$$

Through the arrangement of a correction reactor and a pH sensor and a biomass concentration sensor installed thereon, as well as a correction controller and a correction unit coupled with the correction reactor, the correction signal $K_m$, can be adjusted in each control loop to improve the control effect of the volume of carbon dioxide introduced into the correction reactor, i.e., the control precision of pH value of algae conditioned medium. The correction unit may adjust the correction control amount $C_C$ in a proportional integral mode. At the same time, the correction signal $K_m$ is input into the distribution controller 22, the distribution controller calculates according to the correction signal $K_m$ to obtain the distribution control amount $C_D$, and those skilled in the art would understand that the first control amount $C_1$ is equivalent to the first approximation of the distribution control amount $C_D$, and the correction control amount $C_C$ is equivalent to the second correction of the distribution control amount $C_D$, which may further improve the control effect of the pH value in the distribution reactor compared with the embodiment shown in FIG. 1. The control mode of the distribution control amount and the correction control amount is not limited to the above-mentioned ratio control, and may also use other control algorithms.

Figure 3A:
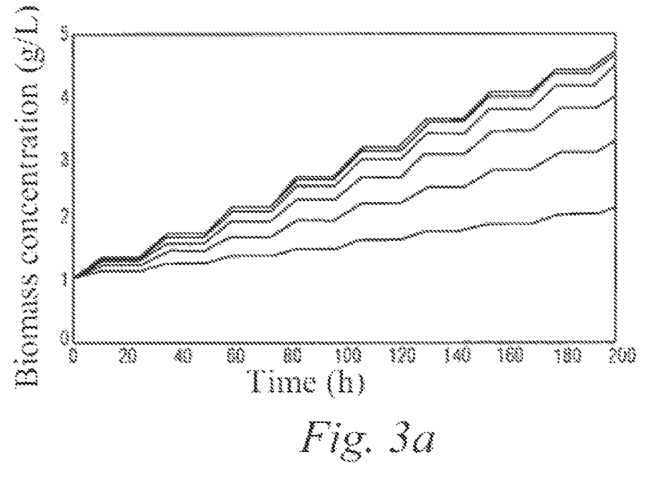
FIG. 3a and FIG. 3b show a simulation curve graph of the operation effect of a monitoring system for the culture of algae in accordance with one embodiment of the present invention.
Figure 3B:
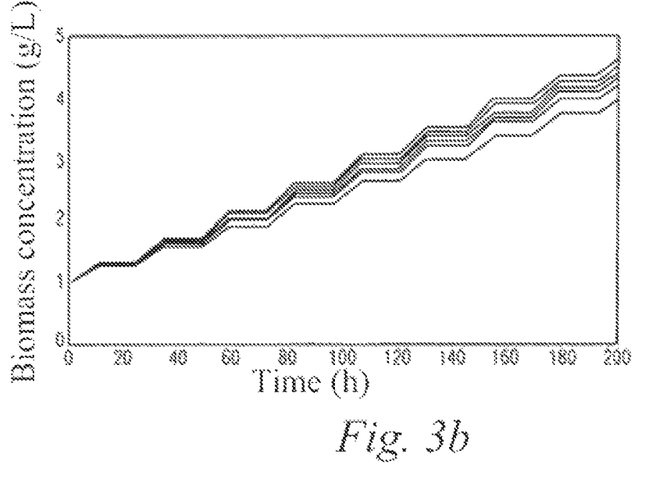

FIG. 3a and FIG. 3b show an operation effect simulation curve graph of the monitoring system for the culture of algae, in which FIG. 3a is the algae biomass obtained by controlling the pH value of algae conditioned medium using a mathematical model for the growth of algae in the prior art, and FIG. 3b is the algae biomass obtained by controlling the pH value of algae conditioned medium using the monitoring system for the culture of algae shown in FIG. 2.

The horizontal coordinate in both figures is culture time, and the vertical coordinate is biomass concentration. In each figure, the curves represent the culture process in reactors, respectively, from the comparison of FIG. 3a and FIG. 3b, it can be seen that in FIG. 3a, different curves have greater difference in slope, indicating greater difference in the biomass of algae in different reactors (from 2.1 g/L to 4.7 g/L), which means that there is greater difference in the control of the pH value in different reactors and some of the reactors are unable to satisfy the requirements of optimized growth of algae In FIG. 3b, different curves have smaller difference in slope, and the biomass of algae in different reactors is high (from 4.0 g/L to 4.7 g/L), which means that the pH value in different reactors may be well controlled to satisfy the requirements of the optimized growth of algae.

The number of correction reactors in the monitoring system for the culture of algae may be increased, and each correction reactor may output a correction signal. The distribution controllers of the distribution reactor may input these correction signals, respectively, and obtain an average of these correction signals as the basis of the distribution control amount output by the distribution controller.

Figure 5:
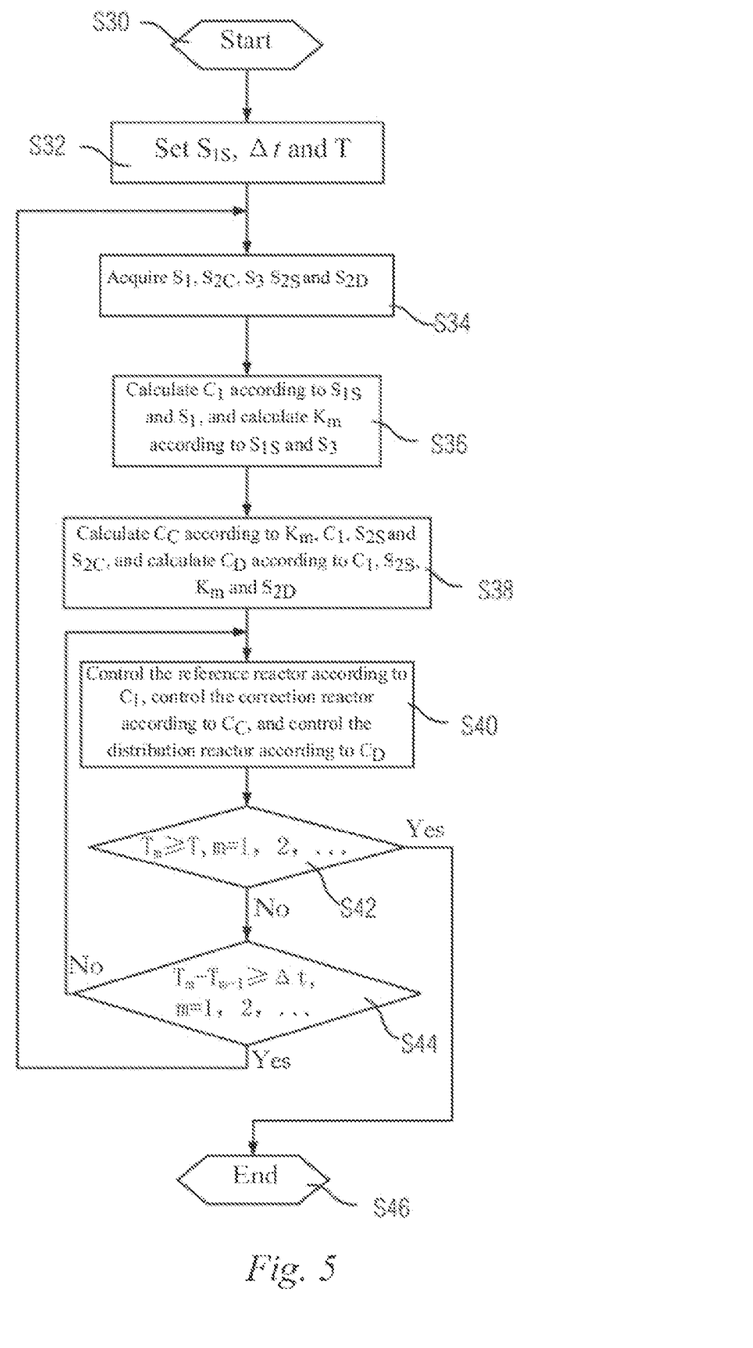
FIG. 5 is a control flowchart of the monitoring system shown in FIG. 2.

FIG. 5 is a control flowchart of the monitoring system shown in FIG. 2. As shown in the figure, the control flow of the monitoring system for the culture of algae starts from step S30.

In step S32, the set value $S_{1S}$, the control cycle $\Delta t$, and the production cycle T of the production process are set. In one embodiment of the culture of algae, the set value $S_{1S}$ is set to 7.0, the control cycle $\Delta t$ is set to one minute, and the production cycle T is set to 200 hours.

In step S34, the pH sensor 12 and the biomass concentration sensor 16 of the reference reactor 110, the pH sensor 12 and the biomass concentration sensor 16 of the correction reactor 130, and the biomass concentration sensor 16 of the distribution reactor 120 perform data sampling, and then the pH sensor 12 of the reference reactor 110 outputs the first signal $S_1$ to the reference control unit 14, the biomass concentration sensor 16 of the reference reactor 110 outputs the biomass concentration reference signals $S_{2S}$ to the correction controller 32 and the distribution controller 22, the pH sensor 12 of the correction reactor 130 outputs the third signal $S_3$ to the correction unit 34, the biomass concentration sensor 16 of the correction reactor 130 outputs the biomass concentration correction signal $S_{2C}$ to the correction controller 32, and the biomass concentration sensor 16 of the distribution reactor 120 outputs the biomass concentration distribution signal $S_{2D}$ to the distribution controller 22.

In step S36, the reference control unit 14 calculates according to the set value $S_{1S}$ and the first signal $S_1$ to obtain the first control amount $C_1$ and outputs the same to the reference reactor 110, the correction controller 32 and the distribution controller 22, and the correction unit 34 calculates according to the set value $S_{1S}$ and the third signal $S_3$ to obtain the correction signal $K_m$ and outputs the same to the correction controller 32 and the distribution controller 22.

In step S38, the correction controller 32 calculates according to the correction signal $K_m$, first control amount $C_1$, biomass concentration reference signal $S_{2S}$ and second parameter correction signal $S_{2C}$ to obtain the correction control amount $C_C$ and outputs the same to the correction reactor 130, and the distribution controller 22 outputs the distribution control amount $C_D$ to the distribution reactor 120 according to the first control amount $C_1$, the correction signal $K_m$, the biomass concentration distribution signal $S_{2D}$ and the biomass concentration reference signal $S_{2S}$.

In step S40, the reference reactor 110 controls the first parameter and the second parameter in the first control amount (in this embodiment, the first parameter is pH value, and the second parameter is biomass concentration) through the first control amount $C_1$, and the correction reactor 130 controls the first parameter therein through the correction control amount $C_C$, and the distribution reactor 120 controls the first parameter therein through the distribution control amount $C_D$.

In step S42, it is determined whether the production cycle T of the production process is reached or not, and if the production cycle is reached, the monitoring process ends at step S46. If the production cycle is not yet reached, the monitoring process proceeds to step S44.

In step S44, the system determines whether the control cycle $\Delta t$ is reached, and if the control cycle is reached, the monitoring process returns to step S34. If the control cycle is not yet reached, the monitoring process returns to step S40.

The above-mentioned control units, comparators and controllers may be independent control devices, and may also be different modules on the same control device. This control device may be a programmable logic controller (PLC), a distribution control system (DCS), an industrial personal computer, etc.

Herein, "first", "second", "third", etc. are only used to distinguish different actuators, signals, etc., and shall not be understood to indicate their sequence and/or degree of importance. "Illustrative" means "acting as an example, an instance or illustration", any diagram and embodiment which is described as "illustrative" herein shall not be interpreted as a more preferred or more advantageous technical solution.

It should be understood that, although the description is given according to each of the embodiments, but not each embodiment only comprises an independent technical solution, this narration manner of the description is only for clarity, and for those skilled in the art, the description shall be regarded as a whole, and the technical solution in each of the embodiments may also be properly combined to form other implementations that may be understood by those skilled in the art.

The series of detailed descriptions set forth above are only specific descriptions directed to the feasible embodiments of the present invention, and are not intended to limit the scope of protection of the present invention; and all the equivalent embodiments or modifications made without departing from the technical spirit of the present invention shall be included in the scope of protection of the present invention.

The invention claimed is:

1. A production process monitoring system for monitoring a set of production parameters in a production process of a plurality of production units which perform in a parallel production operation to culture algae in the production units, said production units comprising at least one reference production unit and at least one distribution production unit, the production process monitoring system comprising:

a first sensor and a second sensor installed on said at least one reference production unit, the first sensor being configured to monitor a first parameter in the set of production parameters in the at least one reference production unit and output a first signal corresponding to the first parameter of the at least one reference production unit, and the second sensor being configured to monitor a second parameter in the at least one reference production unit and output a second parameter reference signal corresponding to the second parameter of the at least one reference production unit;

a reference control unit installed on said at least one reference production unit, said reference control unit being configured to receive a set value and the first signal, and being configured to output a first control amount for controlling the first parameter in the at least one reference production unit to the at least one reference production unit according to the set value and the first signal;

a further second sensor installed on said at least one distribution production unit, said further second sensor being configured to monitor a second parameter in the at least one distribution production unit and output a second parameter distribution signal corresponding to the second parameter of the at least one distribution production unit; and a distribution controller installed on said at least one distribution production unit, said distribution controller being configured to receive an input signal comprising the first control amount, the second parameter reference signal and the second parameter distribution signal being configured to output a distribution control amount to the at least one distribution production unit, and being configured to control a ratio of the distribution control amount to the first control amount to change said ratio of the distribution control amount to the first control amount according to a ratio of the second parameter distribution signal to the second parameter reference signal.

2. The monitoring system of claim 1, wherein the at least one reference production unit further comprises:

at least one correction production unit having a further first sensor and another second sensor, wherein the further first sensor of the at least one correction production unit is further configured to monitor a first parameter in the at least one correction production unit and output a third signal corresponding to the first parameter, and wherein the other second sensor of the at least one correction production unit is further configured to monitor a second parameter in the at least one correction production unit and output a second parameter correction signal corresponding to the second parameter, and wherein the monitoring system further comprises:

a correction unit configured to output a correction signal according to the received third signal and the set value; and a correction controller configured to output a correction control amount to the at least one correction production unit according to the correction signal, the first control amount, the second parameter reference signal and the second parameter correction signal, and further configured to control a ratio of the correction control amount to the first control amount to change said ratio of the correction control amount to the first control amount according to a ratio of the second parameter correction signal to the second parameter reference signal.

3. The monitoring system of claim 2, wherein a computational formula of the correction control amount ($C_C$) is in accordance with the following relationship:

$$C_C = (K_m \times S_{2C}/S_{2S}) \times C_1; \text{ and}$$

a computational formula of the distribution control amount ($C_D$) is in accordance with the following relationship:

$$C_D = (K_m \times S_{2D}/S_{2S}) \times C_1,$$

where $K_m$ represents the correction signal, $S_{2C}$ represents the second parameter correction signal, $S_{2S}$ represents the second parameter reference signal, $S_{2D}$ represents the second parameter distribution signal, and $C_1$ represents the first control amount.

4. The monitoring system of claim 1, wherein the reference control unit comprises:
   a reference comparator configured to output a first difference signal of the difference between the set value and the received first signal; and
   a reference controller configured to determine the first control amount based on the first difference signal.

5. The monitoring system of claim 2, wherein the correction unit comprises:
   a correction comparator configured to output a third difference signal of the difference between the set value and the third signal; and
   a corrector configured to determine the correction control amount based on the third difference signal.

6. The monitoring system of claim 3, wherein a computational formula of the correction signal ($K_m$) is in accordance with the following relationship:

$$K_m = K_{m-1} + K_C \left( (e_m - e_{m-1}) + \frac{\Delta t}{\tau_I} e_m \right),$$

where subscript 'm' represents the $m^{th}$ control loop in which the monitoring system is located, $\Delta t$ represents control cycle, 'e' is the difference between the set value and the third difference signal, and $K_C$ and $\tau_I$ are set constants that are dependent on the correction production unit.

7. The monitoring system of claim 1, wherein the production process is the culture of the algae, and each product unit of the plurality of production units comprises a photobioreactor.

8. The monitoring system of claim 7, wherein the first parameter is the pH value of algae conditioned medium in the photobioreactor and the second parameter is the biomass concentration of the algae conditioned medium in the photobioreactor, and
   wherein the first control amount and the distribution control amount are the volume of carbon dioxide introduced into the algae conditioned medium, and the pH value of the algae conditioned medium is controlled by the volume of carbon dioxide introduced therein.

9. The monitoring system of claim 2, wherein the production process is the culture of algae and each product unit of the plurality of production units comprises a photobioreactor,
   wherein the first parameter is the pH value of algae conditioned medium in the photobioreactor and the second parameter is the biomass concentration of the algae conditioned medium in the photobioreactor,
   wherein the first control amount, the distribution control amount and the correction control amount are the volume of carbon dioxide introduced into the algae conditioned medium, and
   wherein the pH value of the algae conditioned medium is controlled by the volume of carbon dioxide introduced therein.

10. The monitoring system of claim 7, wherein the first parameter is the dissolved oxygen level of algae conditioned medium in the photobioreactor and the second parameter is the biomass concentration of algae conditioned medium in the photobioreactor,
    wherein the first control amount and the distribution control amount are the volume of air introduced into the algae conditioned medium, and
    wherein the dissolved oxygen level of the algae conditioned medium is controlled by the volume of air introduced therein.

11. The monitoring system of claim 2, wherein the production process is the culture of algae and product unit of the plurality of production units comprises a photobioreactor,
    wherein the first parameter is the dissolved oxygen level of algae conditioned medium in the photobioreactor and the second parameter is the biomass concentration of the algae conditioned medium in the photobioreactor,
    wherein the first control amount, the distribution control amount and the correction control amount are the volume of air introduced into the algae conditioned medium, and
    wherein the dissolved oxygen level of the algae conditioned medium is controlled by the volume of air introduced therein.

12. The monitoring system of claim 8, wherein a sensor for measuring the biomass concentration is a near-infrared light sensor.

13. A control method for a monitoring system of claim 1, comprising:
    (i) setting the set value, a control loop and a production cycle of the production process;
    (ii) performing data sampling at the first sensor and the second sensor of the at least one reference production unit and the further second sensor of the at least one distribution production unit; a first signal being output at the first sensor of the at least one reference production unit to the at least one reference control unit, the second parameter reference signal being output at the second sensor of the at least one reference production unit to the distribution controller, the second parameter distribution signal being output at the further second sensor of the at least one distribution production unit to the distribution controller;
    (iii) calculating, at the at least one reference control unit, based on the set value and the first signal to obtain the first control amount and outputting the first control amount to the at least one reference production unit and the distribution controller, the second parameter distribution signal and the second parameter reference signals being calculated at the distribution controller based on the first control amount to obtain the distribution control amount and the distribution control amount being output to the at least one distribution production unit;
    (iv) controlling, at the at least one reference production unit, the first parameter therein through the first control amount, and controlling, at the at least one distribution production unit, the first parameter therein through the distribution control amount;
    (v) determining whether the production cycle of the production process is reached; ending a monitoring process when the production cycle is reached; and proceeding to step (vi) when the production cycle is not yet reached; and (vi) determining whether the control loop is reached; returning to step (ii) when the control loop is reached; and returning to step (iv) when the control loop is not yet reached.

14. The control method as claimed in claim 13, further comprising:
(i) re-setting the set value, control loop and production cycle of the production process;
(ii) performing data sampling at the first sensor and the second sensor of the at least one reference production unit, a further first sensor and another second sensor of a correction production unit, and the further second sensor of the at least one distribution production unit, the first signal to the at least one reference control unit being output at the first sensor of the at least one reference production unit, the second parameter reference signals being output at the second sensor of the at least one reference production unit to a correction controller and the distribution controller, the third signal being output at the further first sensor of the correction production unit to the correction unit, the second parameter correction signal being output at the second sensor of the correction production unit to the correction controller, and the second parameter distribution signal being output at the further second sensor of the at least one distribution production unit to the distribution controller;
(iii) re-calculating, at the at least one reference control unit, based on the set value and the first signal to obtain the first control amount and outputting the first control amount to the at least one reference production unit and the distribution controller; and calculating, at the distribution controller, based on the set value and the third signal to obtain the correction signal and outputting the correction signal to the correction controller and the distribution controller;
(iv) calculating, at the correction controller, based on the first control amount, the second signal, the second parameter reference signal and the correction signal to obtain the correction control amount and outputting the correction control amount to the at least one correction production unit; and calculating, at the distribution controller, based on the first control amount, the correction signal, the second parameter distribution signal and the parameter reference signals to obtain the distribution control amount and outputting the distribution control amount to the at least one distribution production unit;
(v) re-controlling, at the at least one reference production unit, the first parameter therein through the first control amount; re-controlling, at the at least one distribution production unit, the first parameter therein through the distribution control amount; and controlling, at the correction production unit, the first parameter therein through the correction control amount;
(vi) re-determining whether the production cycle of the production process is reached; ending an entire monitoring process when the production cycle is reached; and re-proceeding to step (vii) when the production cycle is not yet reached; and
(vii) re-determining whether the control loop is reached; re-returning to step (ii) when the control loop is reached; and re-returning to step (v) when the control loop is not yet reached.

15. The control method of claim 13, wherein the control loop is in a range of 1 s to 1 h.

\* \* \* \* \*